United States Patent [19]
Hofheinz et al.

[11] Patent Number: 5,596,002
[45] Date of Patent: Jan. 21, 1997

[54] METHOD OF TREATING CHLOROQUINE-RESISTANT MALARIA WITH AMINOQUINOLINE DERIVATIVES

[75] Inventors: Werner Hofheinz, Bottmingen; Catherine Jaquet, Basel; Synèse Jolidon, Blauen, all of Switzerland

[73] Assignee: Hoffmann-La Roche Inc., Nutley, N.J.

[21] Appl. No.: 329,596

[22] Filed: Oct. 26, 1994

[30] Foreign Application Priority Data

Oct. 28, 1993 [CH] Switzerland ............................. 3255/93

[51] Int. Cl.$^6$ .................... A61K 31/47; C07D 215/44; C07D 215/46
[52] U.S. Cl. ............................................. 514/313; 546/163
[58] Field of Search ............................ 546/163; 514/313

[56] References Cited

U.S. PATENT DOCUMENTS 2,594,419  4/1952  Geschickter ............................. 546/163
3,346,579  10/1967  Sheehan ................................... 546/163

OTHER PUBLICATIONS

Singh, "Antimalarials . . . ", *J Med Chem*, vol. 14, No. 4, pp. 283–286, 1971.

*Primary Examiner*—C. Warren Ivy
*Assistant Examiner*—D. Margaret M. Mach
*Attorney, Agent, or Firm*—George W. Johnston; Patricia S. Rocha-Tramaloni

[57] ABSTRACT

Novel aminoquinoline derivatives of the general formula

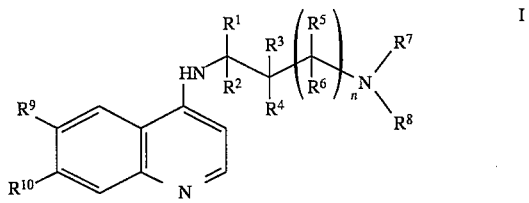

are described. Also described are methods for the treatment of malaria pathogens, particularly chloroquine-resistance malaria pathogens with compounds of formula I or the pharmaceutically acceptable salts and hydrolyzable esters thereof.

10 Claims, No Drawings

METHOD OF TREATING CHLOROQUINE-RESISTANT MALARIA WITH AMINOQUINOLINE DERIVATIVES

SUMMARY AND BACKGROUND OF THE INVENTION

The present invention is directed to aminoquinoline derivatives of the general formula

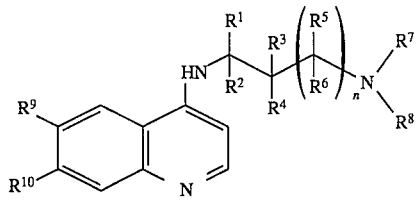

I wherein $R^1$ to $R^6$ are independently selected from hydrogen or alkyl, provided that no more than two substituents from $R^1$ to $R^6$ may be simultaneously alkyl; $R^7$ and $R^8$ signify alkyl, alkenyl or aralkyl, or together with the N atom signify pyrrolidine or piperidine, which optionally can be substituted by alkyl, or octahydroindole or 3-azabicyclo[3,2,2]nonane; and n=0 or 1; or wherein the symbols $R^1$ and $R^3$ signify tri- or tetramethylene; $R^2$ and $R^4$ to $R^6$ signify hydrogen; n=0; and $R^7$ and $R^8$ are defined as above; or wherein the symbols $R^1$ and $R^7$ signify methylene or dimethylene and n=1, or
$R^1$ and $R^7$ signify di- or trimethylene and n=0, or
$R^3$ and $R^7$ signify di- or trimethylene and n=1, or
$R^3$ and $R^7$ signify tri- or tetramethylene and n=0, or
$R^5$ and $R^7$ signify tri- or tetramethylene and n=1, or
$R^1$ and $R^5$ signfly di- or tri-methylene and n=1, and the remaining substituents signify hydrogen, except $R^8$ which signifies alkyl, alkenyl or alkynyl; or wherein the symbols $R^3$ and $R^5$ signify tri- or tetramethylene and n=1; all remaining substituents to $R^6$ signify hydrogen; and $R^7$ and $R^8$ signify alkyl, alkenyl or aralkyl or together with the N atom signify pyrrolidine or piperidine, which optionally can be substituted by alkyl; $R^9$ signifies hydrogen or halogen; and $R^{10}$ signifies halogen or trifluoromethyl, and pharmaceutically acceptable salts and hydrolyzable esters thereof.

These compounds are useful in the treatment and prevention of malaria.

The compounds described above are novel with the exception of the following specific compounds, which are hereinafter referred to as the "Z-compounds":

$N_2$-(7-chloro-quinolin-4-yl)-$N_1,N_1$-dimethyl-ethane-1,2-diamine, $N_2$-(7-chloro-quinolin-4-yl)-$N_1,N_1$-diethyl-ethane-1,2-diamine, $N_3$-(7-chloro-quinolin-4-yl)-$N_1,N_1$-dimethyl-propane-1,3-diamine, $N_3$-(7-chloro-quinolin-4-yl)-$N_1,N_1$-diethyl-propane-1,3-diamine, (7-chloro-quinolin-4-yl)-(2-piperidin-1-yl-ethyl)-amine, (7-chloro-quinnolin-4-yl)-[(1-ethyl-pyrrolidin-2-yl)-methyl]-amine, (7-chloro-quinolin-4-yl)-(1-methyl-pyrrolidin-2-yl-methyl)-amine, (7-chloro-quinolin-4-yl)-(1-methyl-piperidin-2-yl-methyl)-amine and (7-chloro-quinolin-4-yl)-(1-methyl-piperidin-3-yl)-amine.

All of the foregoing compounds including the Z-compounds, have the surprising and newly discovered property that they have an equally good effect not only against chloroquine-sensitive malaria pathogens, but also against chloroquine-resistant malaria pathogens, that is to say, they exhibit no cross-resistance with chloroquine.

Not only the absence of cross-resistance, but also the good activity, which is to some extent better compared with chloroquine, were surprising. Hitherto it had been assumed that cross-resistance exists between chloroquine-like compounds. Only certain bis-quinolines, which contain two quinoline rings and which bear little structural relationship to chloroquine, have a definite activity against chloroquine-resistant malaria pathogens, especially the compounds which have been described by J. L. Vennerstrom (J. L. Vennerstrom et al, J. Med. Chem., 35, 2129–2134 (1992). Further, it had hitherto been assumed that chloroquine analogues having shortened or lengthened side-chains were less active against malaria pathogens compared with chloroquine (R. L. O'Brien and F. E. Hahn, Chloroquin Structural Requirements for Binding to Deoxyribonucleic Acid and Antimalarial Activity, Antimicrob. Agents Chemother, 1965, 315–320).

Simple analogues of chloroquine have therefore hitherto been considered to be uninteresting and not suitable for the treatment for malaria. In contrast to this assumption, it has now been found that the compounds of formula I are outstandingly suitable for the prophylaxis of malaria and for its treatment, especially in cases where the pathogens are resistant to chloroquine.

The objects of the present invention are the use of compounds of formula I and the Z-compounds and of pharmaceutically usable salts and hydrolyzable esters thereof in the control or prevention of malaria, especially in the control of chloroquine-resistant and of chloroquine-sensitive malaria pathogens; the novel compounds of formula I; the manufacture of the compounds of formula I and pharmaceutically acceptable salts and esters thereof, as well as pharmaceutical compositions containing said compounds or salts or hydrolyzable esters thereof, and the manufacture of such pharmaceutical compositions.

DETAILED DESCRIPTION OF THE INVENTION

The term "alkyl" used in the present description denotes straight-chain or branched saturated $C_1$–$C_4$ hydrocarbon residues, for example methyl, ethyl, n-propyl, isopropyl, n-butyl, isobutyl, s-butyl, t-butyl and the like.

Halogen signifies chlorine, bromine, fluorine or iodine.

Compounds in which $R^1$ to $R^6$ are hydrogen or in which one or two of $R^1$ to $R^6$ are independently selected from alkyl and the other substituents are hydrogen, and wherein $R^7$ and $R^8$ are independently selected from alkyl, alkenyl or aralkyl or together with the N atom signify pyrrolidine or piperidine, which optionally can be substituted by alkyl, and n=0 or 1, are especially preferred.

Particularly preferred compounds of general formula I are:

(S)-$N_2$-(7-Chloro-quinolin-4-yl)-$N_1,N_1$-dimethyl-propane-1,2-diamine, (R)-$N_2$-(7-chloro-quinolin-4-yl)-$N_1,N_1$-dimethyl-propane-1,2-diamine, $N_1$-(7-chloro-quinolin-4-yl)-2,$N_2$,$N_2$-trimethyl-propane-1,2-diamine, $N_3$-(7-chloro-quinolin-4-yl)-$N_1$,$N_1$-diethyl-propane-1,3-diamine, (RS)-(7-chloro-quinolin-4-yl)-(1-methyl-piperidin-3-yl)-amine and (RS)-(7-choro-quinolin-4-yl)-(1-methyl-pyrrolidin-3-yl)-amine.

Also preferred are:

(RS)-$N_2$-(7-Chloro-quinolin-4-yl)-$N_1$,$N_1$-dimethyl-propane-1,2-diamine, (RS)-$N_2$-(7-chloro-quinolin-4-yl)-$N_1$,$N_1$-diethyl-propane-1,2-diamine, (S)-$N_2$-(7-chloro-quinolin-4-yl)-$N_1$,$N_1$-diethyl-propane-1,2-diamine, (R)-$N_2$-(7-chloro-quinolin-4-yl)-$N_1$,$N_1$-diethyl-propane-1,2-diamine, (RS)-7-chloro-quinolin-4-yl)-(1-methyl-2-pyrrolidin-1-yl-ethyl)-amine, $N_2$-(7-chloro-quinolin-4-yl)-$N_1$,$N_1$-dimethyl-ethane-1,2-diamine, $N_2$-(7-chloro-quinolin-4-yl)-$N_1$,$N_1$-diethyl-ethane-1,2-diamine, $N_3$-(7-chloro-quinolin-4-yl)-$N_1$,$N_1$-dimethyl-propane-1,3-diamine, (R)-$N_1$-(7-chloro-quinolin-4-yl)-$N_2$,$N_2$-dimethyl-propane-1,2-diamine, (S)-$N_1$-(7-chloro-quinoline-4-yl)-$N_2$,$N_2$-dimethyl-propane-1,2-diamine and (RS)-(7-chloro-quinolin-4-yl)-(1-methyl-pyrrolidin-2-yl-methyl)-amine.

The pharmaceutically acceptable salts includes any salt chemically permissible in the art for the compounds of formula I and applicable to human patients in a pharmaceutically acceptable preparation. Any such conventional pharmaceutically acceptable salt of the compounds of formula I can be utilized. Among the conventional salts which can be utilized there are the base salt, for example, alkali metal salts such as sodium or potassium, alkaline earth metal salts such as sodium or potassium, alkaline earth metal salts such as calcium or magnesium, and ammonium or alkyl ammonium salts.

The novel compounds of formula I can be manufactured in accordance with the invention as follows:

a) reacting quinoline derivatives of the general formula

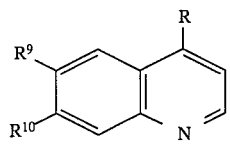

II wherein $R^9$ and $R^{10}$ have the above significances and R signifies a leaving group, with amino compounds of the general formula

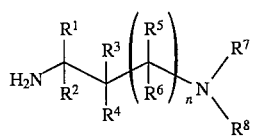

III wherein the substituents $R^1$ to $R^8$ have the above significances, or b) reacting alkylamino-quinoline derivatives of the general formula

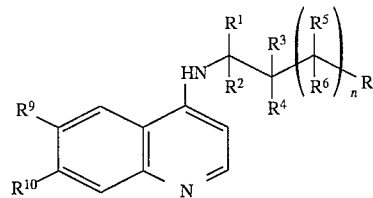

IV wherein $R^1$ to $R^6$ and $R^9$ and $R^{10}$ have the above significances and R signifies a leaving group, with amines of the formula HN$R^7R^8$  V wherein $R^7$ and $R^8$ have the above significances, or c) reacting compounds of formula I in which $R^1$ to $R^6$ as well as $R^9$ and $R^{10}$ have the above significance and $R^7$ and $R^8$ signify hydrogen or one of them signifies hydrogen and the other signifies an alkyl group with alkylating agents which are suitable for the alkylation of amino groups, and d) if desired, converting a basic compound of formula I into a pharmaceutically usable salt by means of an acid.

According to variant a) of the process in accordance with the invention correspondingly substituted quinoline derivatives which contain a leaving group in the 4-position are reacted with amino compounds of general formula III, the substituents having the significances given above and R signifying a leaving group.

Leaving groups are well recognized in the art and conveniently are halogen, O-methylsulphonyl or O-toluene-sulphonyl groups. The reaction is conveniently effected in a temperature range between 120° and 180° C. and in a solvent, with phenol, ethoxyethanol, dimethylacetamide or N-methylpyrrolidine being especially preferred. The reaction time can vary between 2 and 28 hours.

A further possibility for the manufacture of the compounds of general formula I comprises using process variant b).

Conveniently, the compounds of formula IV in which R signifies a leaving group and all other substituents are as defined above is reacted in the form of the hydrochloride of the correspondingly substituted alkylamino-quinoline derivative with an aliphatic or cyclic amine of formula V in a sealed tube, whereby the amine can simultaneously serve as the solvent. The reaction can take up to 24 h. The preferred temperature range embraces temperatures between 90° and 110° C. This reaction can also be effected in solvents in which both reaction partners are soluble, for example in DMF, DMA, N-methylpyrrolidone or acetonitrile. The conversion into a pharmaceutically usable salt is effected by adding an acid. HCl is especially preferred because of the physiological compatibility of the hydrochloride. Convenient solvents which are especially suitable are: isopropanol, diethyl ether or dioxan.

Alkylating agents which are suitable for process variant c) are, for example, formaldehyde in combination with formic acid, in which case the reaction is preferably carried out in excess formic acid. Other useful alkylating agents include combinations of aliphatic or aromatic aldehydes with complex hydrides such as sodium borohydride or sodium cyanoborohydride. Such reactions can be conveniently carried out in alcoholic or aqueous solutions.

The quinoline derivatives of general formula II required for synthesis variant a) are commercial products or can be prepared according to methods known per se, for example 7-chloro-4-hydroxyquinoline can be converted with phosphorus oxybromide into 7-chloro-4-bromo-quinoline.

The aliphatic or cyclic amines of general formula III are also available commercial products or can be prepared according to methods known per se. Conveniently, the starting point can be a cyclic amine, for example pyrrolidine or piperidine, or an aliphatic amine, e.g. dimethylamine or diethylamine, which can be reacted with nitroethane or 2-nitropropane. The resulting nitro compound can subsequently be reduced according to methods known per se, e.g. by hydrogenation with Raney-nickel, to the compounds of general formula III.

A further possibility for the preparation of the compounds of general formula III comprises converting cycloalkane oxides with diethylamine and perchlorates into 2-(diethylamio)-cycloalkanols. These are conveniently dissolved, without further purification, in THF and treated with phthalimide and triphenylphosphine and subsequently stirred at room temperature for several hours. After purification the resulting N,N-diethyl-2-phthalimido-cycloalkylamine is saponified with concentrated hydrochloric acid.

In analogy thereto, in place of diethylamine and other aliphatic amines there can also be used, for example, cyclic amines such as pyrrolidine. When cyclic amines, for example piperidine, are reacted with acrylonitrile there is obtained the corresponding propionitrile which can be hydrogenated to the corresponding propylamine in the presence of platinum dioxide at room temperature (RT) under pressure of 10 bar.

The corresponding alkylamino-quinoline derivative of general formula W in which the leaving group signifies a halogen group, preferably chlorine, required as the starting material for synthesis variant b) can conveniently be prepared as follows:

A suspension of the corresponding quinolinamino-ethanol, which can be prepared according to a synthesis of R. C. Elderfield, J. Am. Chem. Soc. 68, 1250 (1946), is treated with thionyl chloride, whereby the reaction temperature should not exceed 30° C. Subsequently, the mixture is stirred at RT for 1 h., evaporated to dryness and purified.

As mentioned earlier, the aminoquinoline derivatives of general formula I and their pharmaceutically usable salts have extremely valuable pharmacological properties.

Their activity against not only chloroquine-resistant, but also chloroquine-sensitive malaria pathogens will be evident from the following Tables:

Test method for the determination of the activity against *P. falciparum* in vitro The preparations of the present invention were tested on intraerythrocytary stages of *P. falciparum* from asynchronous cultures according to the method of Desjardin et al. (Desjardins, R. E. et al: Quantitative assessment of antimalarial activity in vitro by a semiautomated microdilution technique. Antimicrob. Agents Chemother. 16, 710–718, (1979)).

The culture medium consisted of RPMI 1640 with the addition of 25 mM HEPES, 25 mM $NaHCO_3$, 100 mg/ml neomycin and 10% human serum ($A^+$). Human-$A^+$ erythrocytes were used as the *P. falciparum* host cells. The parasites were maintained at 37° C. in an atmosphere of 3% $O_2$, 4% $CO_2$, 93% $N_2$ and at 95% relative humidity.

In order to determine the activity, the preparations were dissolved in DMSO, pre-diluted in the culture medium to a suitable starting concentration and subsequently titrated-out into microtitre plates in the 2nd stage over 6–7 steps. After the addition of the parasite culture (0.7% parasitemia in 2.5% erythrocyte suspension), the test plates were incubated under the conditions given above for 48 h–72 h. The parasite growth in the different preparation concentrations was determined using [G-$^3$H]-hypoxanthin incorporation compared to untreated control cultures on the same test plates. The 50% growth inhibition (IC50) was calculated according to logit regression analysis from the resulting dosage-activity curve.

The preparations were tested on at least one chloroquine-resistant and one chloroquine-sensitive *P. falciparum* strain. Additional sensitive and resistant strains were also included for further characterization.

Test method for the determination of the activity against *Plasmodium berghei* in vivo The preparations according to the present invention were tested on mice infected with malaria pathogens (*Plasmodium berghei*). Male albino mice (IBM:MORO(SPF), FUELLINSDORF) weighing about 25 g were used as the test animals. They were kept in climatized rooms at 21°–22° C. in groups of 5 animals per cage. They received ad libitum a diet feed with a low PABA content ("NAFAG FUTTER" No. 9009 PAB-45, PABA content 45 mg/kg) and drinking water. On the first day of the test (D0) the test animals were infected with *Plasmodium berghei* (strain ANKA). For this there was used heparinized blood of a donor mouse with about 30% parasitemia, which was diluted with physiological saline such that it contains $10^8$ parasitized erythrocytes per ml. 0.2 ml of this suspension was injected intravenously (i.v.) into the mice to be treated and into the control mice. In untreated control animals the parasitemia normally reaches 30–40% on the third day after the infection (D+3) and the test animals die between days +5 and +7.

The substances to be tested were dissolved or suspended in distilled water or in a mixture of 7% Tween 80, 3% alcohol (96%) and water. Usually, 0.25 ml of this solution or suspension was administered once subcutaneously and perorally to groups of 5 test animals. Treatment was effected 24 hours after the infection. 10 control animals were treated in the same manner with solvent or suspension medium per test.

All substances were tested in a first test in a single dosage of 10 mg/kg. Only those substances which in this test (10 mg/kg) had shown a parasitaemia reduction of 90% were used for the titration.

48 hours after the treatment (D+3), blood smears were prepared from all animals using blood from tail veins and were stained with Giemsa. The average erythrocyte infection rate (parasitemia in %) in the control groups as well as in the groups which had been treated with the test compounds was determined by counting under a microscope. The difference in the average values of the infection rates of control group (100%) and treated groups was calculated and expressed as a percentage reduction (GI %). The ED50 or ED90 was determined mathematically by means of the JMP programme (nonlinear fit). The ED50 (ED90) in mg/kg is that dose which after single administration reduces the average erythrocyte infection rate by 50% (90%) in comparison to the control group.

Table 1 below contains the IC50 values measured in vitro for the growth inhibition of chloroquine-sensitive and chloroquine-resistant strains of the human pathogenic *Plasmodium falciparum*.

Table 2 below contains data with respect to the activity measured against *Plasmodium berghei* in mice: GI % is the percentage reduction in the parasitemia after a single dose of 10 mg/kg of the test substance administered perorally (po) or subcutaneously (sc); ED50 and ED90 are the effective doses of the test substance administered perorally or subcutaneously.

TABLE 1

| Example No. | Chloroquine-sensitive strain, IC50 (ng/ml) | | | | | Chloroquine-resistant strain, IC50 (ng/ml) | | | | | | |
|---|---|---|---|---|---|---|---|---|---|---|---|---|
| | NF54 | FCH5C2 | HB3 | RFMEF3 | Ro7 3 | RFCR3 | ItG2 F6 | Indo | K1 | W2 | 7G8 | W2 Mef |
| 1 | 4 | 8 | 7 | 7 | 5 | 15 | 4 | 8 | 9 | 9 | 9 | 7 |
| 2 | 7 | 7 | 7 | 7 | 6 | 8 | 5 | 6 | 14 | 8 | 8 | 9 |
| 3 | 7 | 7 | 5 | 7 | 4 | 8 | 5 | 6 | 12 | 7 | 7 | 11 |
| 4 | 7 | 8 | 8 | 7 | 4 | 9 | 5 | 8 | 15 | 15 | 7 | 14 |
| 5 | 4 | 9 | 6 | | | 6 | 4 | 4 | 7 | 7 | 7 | 9 |
| 6 | 5 | 8 | 8 | | | 8 | 5 | 4 | 9 | 8 | 9 | 8 |
| 7 | 4 | 7 | 6 | | | 7 | 5 | 4 | 8 | 7 | 8 | 8 |
| 8 | 5 | 9 | 7 | 9 | 4 | 10 | 4 | 5 | 11 | 11 | 7 | 9 |
| 9 | 11 | 15 | 14 | 12 | 11 | 17 | 17 | 18 | 32 | 31 | 30 | 25 |
| 10 | 7 | 5 | 8 | 6 | 7 | 18 | 7 | 16 | 17 | 13 | 15 | 15 |
| 11 | 5 | 7 | 6 | 6 | 5 | 13 | 6 | 10 | 18 | 15 | 9 | 9 |
| 11a | 7 | 7 | 6 | 7 | 4 | 18 | 8 | 15 | 15 | 17 | 14 | 15 |
| 12 | 6 | 9 | 7 | 8 | 7 | 15 | 8 | 12 | 10 | 15 | 15 | 9 |
| 12a | 7 | 8 | 10 | 8 | 7 | 11 | 5 | 11 | 9 | 9 | 8 | 6 |
| 13 | 30 | 28 | 38 | 27 | 30 | 58 | 25 | 40 | 47 | 34 | 39 | 41 |
| 14 | 9 | 8 | 9 | 6 | 4 | 8 | 6 | 10 | 21 | 20 | 7 | 14 |
| 15 | 2 | 5 | 3 | | | 5 | 3 | 3 | 6 | 7 | 7 | 12 |
| 16 | 3 | 6 | 5 | | | 8 | 5 | 4 | 9 | 9 | 9 | 9 |
| 17 | 3 | 4 | 6 | 8 | 6 | 11 | 7 | 7 | 15 | 14 | 14 | 14 |
| 18 | 4 | 4 | 8 | 8 | 7 | 8 | 7 | 7 | 14 | 11 | 12 | 12 |
| 19 | 7 | 5 | 4 | 5 | 3 | 10 | 6 | 7 | 9 | 10 | 7 | 11 |
| 19a | 6 | 7 | 6 | 7 | 5 | 11 | 5 | 8 | 9 | 10 | 8 | 6 |
| 20 | 3 | 7 | 4 | 4 | 7 | 14 | 7 | 8 | 10 | 11 | 15 | 14 |
| 21 | 21 | 35 | 33 | 35 | 28 | 54 | 28 | 31 | 34 | 57 | 49 | |
| 22 | 14 | 17 | 20 | 18 | 11 | 20 | 14 | 16 | 22 | 11 | 29 | 23 |
| 23 | 6 | 6 | 7 | 7 | 4 | 10 | 6 | 8 | 15 | 15 | 8 | 13 |
| 24 | 7 | 7 | 7 | 7 | 4 | 9 | 6 | 8 | 15 | 15 | 7 | 9 |
| 25 | 8 | 8 | 10 | 8 | 5 | 14 | 8 | 15 | 22 | 26 | 11 | 16 |
| 26 | 7 | 8 | 8 | 9 | 5 | 8 | 6 | 9 | 15 | 15 | 8 | 13 |
| 27 | 8 | 10 | 9 | 7 | 3 | 15 | 7 | 9 | 18 | 19 | 7 | 14 |
| 28 | 7 | 14 | 11 | 9 | 5 | 16 | 6 | 9 | 16 | 18 | 9 | 15 |
| 29 | 6 | 6 | 7 | 5 | 3 | 11 | 6 | 7 | 16 | 15 | 5 | 11 |
| 30 | 7 | 9 | 10 | 8 | 11 | 16 | 7 | 7 | 14 | 15 | 15 | 8 |
| 31 | 5 | 5 | 5 | 6 | 5 | 14 | 7 | 7 | 11 | 14 | 9 | 7 |
| 32 | 7 | 9 | 9 | 8 | 7 | 16 | 10 | 15 | 16 | 15 | 15 | 13 |
| 33 | 8 | 15 | 15 | 16 | 10 | 18 | 9 | 14 | 14 | 21 | 18 | 15 |
| 33a | 7 | 8 | 7 | 7 | 5 | 9 | 5 | 9 | 8 | 9 | 9 | 7 |
| 33b | 8 | 11 | 12 | 8 | 4 | 10 | 17 | 9 | 17 | 9 | 18 | 18 |
| 33c | 8 | | | | | | | | 24 | | | |
| 33d | 8 | | | | | | | | 23 | | | |
| 33e | 12 | | | | | | | | 53 | | | |
| 33f | 12 | | | | | | | | 41 | | | |
| 33g | 5 | | | | | | | | 17 | | | |
| 33h | 7 | | | | | | | | 18 | | | |
| Chloroquine diphosphate | 8 | 12 | 11 | 14 | 8 | 130 | 68 | 52 | 114 | 123 | 81 | 79 |

TABLE 2

| Example No. | Activity in vivo | | |
|---|---|---|---|
| | GI % at 10 mg/kg (po) | GI % at 10 mg/kg (sc) | ED50 mg/kg (po) |
| 1 | 99.9 | 99.9 | 2.3 |
| 2 | 99.8 | 99.9 | 3.2 |
| 5 | 99.5 | 99.0 | 3.3 |
| 6 | 99.0 | 99.0 | 3.5 |
| 9 | 99.0 | 99.6 | 4.4 |
| 10 | 99.0 | 99.0 | 6.4 |
| 11 | 99.9 | 99.9 | 2.2 |
| 11a | 99.0 | 99.6 | 4.5 |
| 12a | 91.0 | 91.0 | 4.8 |
| 15 | 99.8 | 99.9 | 2.0 |
| 16 | 99.9 | 99.9 | 2.0 |
| 17 | 95.0 | 99.0 | 4.6 |
| 18 | 83.0 | 96.0 | 6.9 |
| 19 | 99.0 | 99.6 | 5.3 |
| 19a | 99.9 | 99.9 | 2.4 |
| 20 | 99.9 | 99.9 | 4.4 |
| 33 | 97.0 | 97.0 | 5.9 |
| 33a | 99.7 | 99.9 | 3.3 |
| 33b | 99.9 | 99.9 | |
| 33c | 99.9 | 99.9 | 1.9 |
| 33d | 99.9 | 99.9 | 2.2 |
| 33e | 99.8 | 99.9 | 3.1 |
| 33f | 99.8 | 99.9 | 2.8 |
| Chloroquine diphosphate | 99.9 | 99.9 | 2.4 |

In accordance with one embodiment of this invention, a therapeutically effective amount of a compound of formula I or Z-compound or its pharmaceutically acceptable salts is administered to a malaria infected patient to treat said patent, including retarding further development of the disease. For such treatment, a compound of formula I or Z-compound or its pharmaceutically acceptable salts is administered systemically in the form of a composition containing a therapeutically effective amount of said compound and a pharmaceutically acceptable carrier compatible with said compound. In preparing such a composition, any conventional pharmaceutically acceptable carrier can be utilized. When the pharmaceutical composition is administered orally, it is generally administered at regular intervals preferably at mealtimes or once daily. The compounds of formula I are relatively non-toxic when administered orally.

The treatment of malaria infected hosts, according to the present invention, may be effected with a compound of formula I alone or in combination with other active compounds.

In accordance with this invention, the aforementioned compounds of formula I or Z-compounds, or their pharmaceutically acceptable salts are useful in pharmaceutically acceptable compositions. These pharmaceutical compositions of the invention contain said compound of formula I or Z-compound, or its pharmaceutically acceptable salts, in association with a compatible pharmaceutically acceptable carrier material. Any conventional carrier material can be utilized. The carrier material can be an organic or inorganic inert carrier material, for example one that is suitable for oral administration. Suitable carriers include water, gelatin, gum arabic, lactose, starch, magnesium stearate, talc, vegetable oils, polyalkylene-glycols, petroleum jelly and the like. Furthermore, the pharmaceutical preparations may also contain other pharmaceutically active agents. Additional additives such as flavoring agents, preservatives, stabilizers, emulsifying agents, buffers and the like may be added in accordance with accepted practices of pharmaceutical compounding.

The pharmaceutical preparations can be made up in any conventional form including: (a) a solid form for oral administration such as tablets, capsules, pills, powders, granules, and the like. The pharmaceutical preparations may be sterilized and/or may contain adjuvants such as preservatives, stabilizers, wetting agents, emulsifiers, salts for varying the osmotic pressure and/or buffers.

A preferred oral dosage form comprises tablets, capsules of hard or soft gelatin methylcellulose or of another suitable material easily dissolved in the digestive tract. The oral dosages contemplated in accordance with the present invention will vary in accordance with the needs of the individual patient as determined by the prescribing physician. Generally, however, a daily dosage of from about 1 mg. to about 50 mg. per Kg. of body weight and preferably from about 5 mg. to about 25 mg. per Kg. of body weight of the patent is utilized. This dosage may be administered according to any dosage schedule determined by the physician in accordance with the requirements of the patient.

It is likewise within the preview of the present invention to incorporate the therapeutically active substance enumerated herein in any desired mount for enteral administration within the oral unit dosage form. It is preferred, however, to formulate preparations containing the active substance of the present invention in such a manner that each dose forms contains from bout 50 mg. to about 1000 mg, preferably 250 mg., with suitable therapeutically inert fillers and diluents. It is especially preferred to incorporate such a dosage into soft gelatin capsules and tablets.

The dosage for treatment typically depends on the route of administration, the age, weight and degree of malarial infection of the patient.

EXAMPLES

The following Examples are illustrative of the present invention and are not intended to limit its scope in any manner. All temperatures are given in degrees Celsius. The 250 Mz-1H-NMR spectra were taken at room temperature; chemical compounds $\delta$ (ppm) relative to $\delta$ (TMS)=0.0 ppm.

Example 1

(RS)-$N_2$-(7-Chloro-quinolin-4-yl)-$N_1$, $N_1$-dimethyl-propane-1,2-diamine 5 g of 4,7-dichloroquinoline, 6.5 ml 1-N,N-dimethylamino-2-propylamine and 0.8 g of phenol were reacted at 140° C. for 6 hours. After cooling 40 ml of water were added, the mixture was adjusted to pH 12 using concentrated sodium hydroxide solution and extracted three times with 150 ml of ethyl acetate each time. The residue remaining after evaporation of the solvent was recrystallized 1× from isopropanol and 1× from acetonitrile. 3.48 g of colorless crystals were obtained, m.p.: 168°–170° C.

$^1$H-NMR in CDCl$_3$, $\delta$ (ppm): 1.29 (d. J=7 Hz, 3H), 2.24 (s, 6H), 2.36 (dd, J=6 Hz and 12.5 Hz, 1H), 2.59 (dd, J=9 Hz and 12.5 Hz, 1H), 3.62 (m, 1H), 5.90 (broad, 1H), 6.44 (d, J=6 Hz, 1H), 7.34 (dd, J=3 Hz and 9 Hz, 1H), 7.74 (d, J=9 Hz, 1H), 7.95 (d, J=3 Hz, 1H), 8.53 (d, J=6 Hz, 1H).

Except as is otherwise specified, the following compounds can be prepared in a manner analogous to Example 1 above:

Example 2

(RS)-$N_2$-(7-Chloro-quinolin-4-yl)-$N_1$, $N_1$-diethyl-propane-1,2-diamine 3.91 g of base from 5 g of 4,7-dichloroquinoline and 6.56 g of 1-N,N-diethylamino-2-propylamine; colourless crystals from acetonitrile, m.p.: 90°–92° C.

$^1$H-NMR in CDCl$_3$, $\delta$ (ppm): 1.01 (t, J=7 Hz, 6H), 1.30 (d, J=6.5 Hz, 3H), 2.4–2.7 (m, 6H), 3.57 (m, 1H), 6.13 (br., 1H), 6.44 (d, J=6 Hz, 1H), 7.36 (dd, J=3 Hz and 9 Hz, 1H), 7.70 (d, J=9 Hz, 1H), 7.95 (d, J=3 Hz, 1H), 8.53 (d, J=6 Hz, 1H).

The dihydrochloride was obtained by adding HCl to a solution in isopropanol; colourless crystals, m.p.: 268°–270° C.

Example 3

(RS)-(7-Chloro-quinolin-4-yl)-(1-methyl-2-pyrrolidin-1-yl-ethyl)-amine 3.36 g of base from 3.18 g of 4,7-dichloroquinoline and 4.12 g of 2-(pyrrolidin-1-yl-propyl)-amine; colourless crystals from acetonitrile, m.p.: 160°–163° C.

$^1$H-NMR in CDCl$_3$, $\delta$ (ppm): 1.32 (t, J=7 Hz, 3H), 1.75 (m, 4H), 2.55 (m, 5H), 2.83 (dd, J=9 Hz and J=12 Hz, 1H), 3.67 (m, 1H), 5.92 (br., 1H), 6.44 (d, J=6 Hz, 1H), 7.35 (dd, J=3 Hz and 9 Hz, 1H), 7.72 (d, J=9 Hz, 1H), 7.95 (d, J=3 Hz, 1H), 8.52 (d, J=6 Hz, 1H).

The dihydrochloride was obtained in the form of colourless crystals which decomposed at 143° by the dropwise addition of a solution of the base in isopropanolic hydrochloric acid (0.35N) to a 4-fold volume of diethyl ether.

Example 4

(RS)-(7-Chloro-quinolin-4-yl)-(1-methyl-2-piperidin-1-yl-ethyl)-amine 3.62 g from 5.22 g of 4,7-dichloroquinoline and 7.5 g of 2-(piperidin-1-yl-propyl)-amine; colourless crystals from ethanol, m.p.: 168°–171° C.

$^1$H-NMR in CDCl$_3$, δ (ppm): 1.30 (d, J=6.5 Hz, 3H), 1.3–1.6 (m, 6H). 2.3–2.6 (m, 6H), 3.62 (m, 1H), 6.20 (broad, 1H), 6.44 (d, J=6 Hz, 1H), 7.39 (dd, J=3 Hz and 9 Hz, 1H), 7.75 (d, J=9 Hz, 1H), 7.95 (d, J=3 Hz, 1H), 8.53 (d, J=6 Hz, 1H).

Example 5

$N_2$-(7-Chloro-quinolin-4-yl)-$N_1,N_1$-dimethyl-ethane-1,2-diamine 1.09 g from 5.9 g of 4,7-dichloroquinoline and 5.3 g of 2-dimethylamino-ethylamine; colorless crystals from ethyl acetate, m.p.: 122°–124° C.

$^1$H-NMR in CDCl$_3$, δ (ppm): 2.30 (s, 6H), 2.68 (m, 2H), 3.28 (m, 2H), 5.91 (br.t, 1H), 6.37 (d, J=5.5 Hz, 1H), 7.36 (dd, J=2.5 Hz and 9 Hz, 1H), 7.71 (d, J=9 Hz, 1H), 7.95 (d, J=2.5 Hz, 1H), 8.53 (d, J=5.5 Hz, 1H).

Example 6

$N_2$-(7-Chloro-quinolin-4-yl)-$N_1,N_1$-diethyl-ethane-1,2-diamine

From 4,7-dichloroquinoline and 2-(N,N-dimethylamino)-ethylamine; colourless crystals from isopropanol, m.p.: above 250°0 C.

$^1$H-NMR in DMSO-d$_6$/D$_2$O, δ (ppm): 1.28 (t, J=7.5 Hz, 6H), 3.28 (q, J=7.5 Hz, 4H), 3.49 (t, J=Hz, 2H), 4.00 (t, J=Hz, 2H), 7.06 (d, J=7 Hz, 1H), 7.75 (dd, J=2 Hz and 9 Hz, 1H), 8.02 (d, J=2 Hz, 1H), 8.59 (d, J=7 Hz, 1H), 8.65 (d, J=9 Hz, 1H).

Example 7

(7-Chloro-quinolin-4-yl)-(2-pyrrolidin-1-yl-ethyl)-amine 3.37 g of base from 3.96 g of 4,7-dichloroquinoline and 5 ml of 1-(2-aminoethyl)-pyrrolidine. Prior to recrystallization the crude product was purified by filtration with ethyl acetate over 300 g of aluminium oxide (activity grade II). From 400 ml of eluate we obtained yellowish crystals that recrystallized from 95 ml of acetonitrile, yielding 3.37 g of colourless crystalline product, m.p.: 134°–136° C.

$^1$H-NMR in CDCl$_3$, δ (ppm): 1.83 (m, 4H), 2.59 (m, 4H), 2.87 (dd, J=6 Hz and 7 Hz, 2H), 3.33 (m, 2H), 5.92 (broad 1H), 6.38 (d, J=6 Hz, 1H), 7.36 (dd, J=3 Hz and 9 Hz, 1H), 7.70 (d, J=9 Hz, 1H), 7.95 (d, J=3 Hz, 1H), 8.53 (d, J=6 Hz, 1H).

The dihydrochloride was obtained in the form of colourless crystals, m.p.: 212°–213° C., by adding HCl to a solution of the base in isopropanol.

Example 8

(7-Chloro-quinolin-4-yl)-(2-piperidin-1-yl-ethyl)-amine 3.57 g of base from 3.96 g of 4,7-dichloroquinoline and 4.8 g of 1-(2-aminoethyl)-piperidine (reaction duration, 5 hours at 140° C.); yellowish crystals from acetonitrile, m.p.: 148°–151° C.

$^1$H-NMR in CDCl$_3$; δ (ppm): 1.45–1.7 (m, 6H), 2.46 (m, 4H), 2.72 (t, J=6 Hz, 2H), 3.29 (m, 2H), 6.12 (br., 1H), 6.36 (d, J=6 Hz, 1H), 7.38 (dd, J=2.5 Hz and 8.5 Hz, 1H), 7.67 (d, J=8.5 Hz, 1H), 7.95 (d J=2.5 Hz, 1H), 8.53 (d, J=6 Hz).

Example 9

(1RS,2RS)-$N_1$-(7-Chloro-quinolin-4-yl)-$N_2$,$N_2$-diethyl-cyclohexane-1,2-diamine 11.3 g of base from 15.2 g of 4,7-dichloroquinoline and 13.4 g of 2-(diethylamino)-cyclohexylamine (reaction duration, 16 hours at 140° C.); colourless crystals from acetonitrile, m.p.: 110°–114° C.

$^1$H-NMR in CDCl$_3$, δ (ppm): 0.98 (t, J=7 Hz, 6H), 1.1–145 (m, 5H), 1.75–2.0 (m, 3H), 2.38 (m, 2H), 2.54 (m, 2H), 2.70 (m, 1H), 3.10 (m, 1H), 6.43 (d, J=6 Hz, 1H), 6.55 (br.s, 1H), 7.36 (dd, J=2.5 Hz and 9 Hz, 1H), 7.71 (d, J=9 Hz, 1H), 7.94 (d, J=2.5 Hz, 1H), 8.52 (d, J=6 Hz, 1H).

The dihydrochloride was obtained from isopropanolic hydrochloric acid; colourless crystals from acetonitrile, dec. at 198° C.

Example 10

(1RS,2RS)-(7-Chloro-quinolin-4-yl)-(2pyrrolidin-1-yl-cyclohexyl)-amine 3.87 g from 3.6 g of 4,7-dichloroquinoline and 3.06 g of (2-pyrrolidin-1-yl-cyclohexyl)-amine (reaction duration 24 hours at 120° C.); colourless crystals from acetonitrile/ethanol, m.p.: 228°–231° C.

$^1$H-NMR in DMSO-d$_6$, δ (ppm): 1.25–2.0 (m, 12H), 2.22 (m, 1H), 3.11 (m, 1H), 3.40 (m, 1H), 3.98 (m, 1H), 4.47 (m, 1H), 7.16 (d, J=7.5 Hz, 1H), 7.75 (dd, J=2.5 Hz and 9.5 Hz, 1H), 8.12 (d, J=2.5 Hz, 1H), 8.64 (d, J=7.5 Hz, 1H), 8.98 (d, J=9.5 Hz, 1H), 9.65 (d, J=9.5 Hz, 1H), 10.15 (br.s, 1H). 14.63 (br.s, 1H).

Example 11

(1RS,2RS)-$N_1$-(7-Chloro-quinolin-4-yl)-$N_2$,$N_2$-diethyl-cyclopentane-1,2-diamine 8.16 g of base from 16 g of 4,7-dichloroquinoline and 12.7 g of 2-(diethylamino)cyclopentylamine (16 hours reaction duration at 140° C.). By addition of isopropanolic hydrochloric acid to a solution of the diamine in isopropanol were precipitated 7.84 g of dihydrochloride; colourless crystals from acetonitrile/ethanol, m.p.: 186°–190° C.

$^1$H-NMR in DMSO-d$_6$, δ (ppm): 1.45 (d, J=6 Hz, 6H), 1.8–2.4 (m, 6H), 2.56 (m, 1H), 3.1–3.5 (m, 4H), 5.20 (m, 2H), 6.90 (d, J=7.5 Hz, 1H), 7.45 (dd, J=2.5 Hz and 9.5 Hz, 1H), 8.15 (d, J=2.5 Hz, 1H), 8.24 (d, J=7.5 Hz, 1H), 9.41 (d, J=9.5 Hz, 1H), 11.55 (br.s, 1H). 14.55 (br.s, 1H).

Example 11a (1RS,2RS)-N$_1$-(7-Chloro-quinolin-4-yl)-
(2-pyrrolidin-1-yl-cyclopentyl)-amine 1.78 g of base from 3.56 g of 4,7-dichloroquinoline and 2.79 g of 2-pyrrolidin-1-yl)-cyclopentylamine.

C$_{18}$H$_{22}$ClN$_3$ (315.85):

Calc.: C 68.45%, H 7.02%, Cl 11.22%, N 13.30% Found: C 68.32%, H 7.00%, C 11.36%, N 13.11%

By addition of isopropanolic hydrochloric acid to a solution of the diamine in isopropanol were obtained 1.64 g of dihydrochloride; colourless crystals from acetonitrile/ethanol, m.p.: 173° C. (dec.). $^1$H-NMR in DMSO-d6, δ (ppm): 1.7–2.0 (m, 8H), 2.3–2.4 (m, 2H), 3.09 (m, 2H), 3.53 (m, 2H), 4.40 (m, 1H), 4.79 (m, 1H), 7.01 (d, 1H, J=7 Hz), 7.79 (dd, J=2.5 Hz and 9 Hz, 1H), 8.11 (d, J=2.5 Hz, 1H), 8.66 (d, J=7 Hz, 1H), 9.04 (d, J=9Hz, 1H), 9.86 (d, J=7.5 Hz, 1H), 11.75 (br.s, 1H) 14.55 (br.s, 1H).

Example 12

(7-Chloro-quinolin-4-yl)-(1-ethyl-pyrrolidin-2-yl-methyl)-amine 9.64 g of base from 8.5 g of 4,7-dichloroquinoline and 11 g of 2-(aminomethyl)-1-ethyl-pyrrolidine. Prior to recrystallization the crude reaction product was purified by chromatography on 400 g of aluminium oxide (activity grade II); a 1:1 mixture of ethyl acetate and hexane was used as the eluent. After a fore-run of 400 ml the product was eluted with 1.5 l of eluent and yielded, after recrystallization from 120 ml of hexane, 9.64 g of colourless crystals; m.p.: 85°–86° C.

Thereafter, 12 g of colourless crystalline dihydrochloride, m.p. 239°–240° C., were obtained by dissolution of the above product in 15 ml of isopropanol, addition of 20 ml of 3.6N isopropanolic hydrochloric acid and dropwise addition to 100 ml of diethyl ether.

$^1$H-NMR in DMSO-d$_6$, δ (ppm): 1.28 (t, J=7.5 Hz, 3H), 1.95 (m, 3H), 2.27 (m, 1H), 3.16 (m, 2H), 3.48 (m, 2H), 3.88 (m, 1H), 4.14 (m, 2H), 7.09 (d, J=8 Hz, 1H), 7.78 (dd, J=3 Hz and 9 Hz, 1H), 8.24 (d, J=3 Hz, 1H), 8.69 (d, J=8 Hz, 1H), 8.94 (d, J=9 Hz, 1H), 10.08 (t, J=6 Hz, 1H), 11.20 (br.s, 1H). 14.80 (br.s, 1H).

Example 12a (7-Chloro-quinolin-4-yl)-(1-methyl-pyrrolidin-2-yl-methyl)-amine Analogously to Example 12 there were obtained 60 mg of base from 2.91 g of 4,7-dichloroquinoline and 1.68 g of 2-(aminomethyl)-1-methyl-pyrrolidine; colourless crystals from hexane, m.p.: 114°–116° C.

$^1$H-NMR in DMSO-d$_6$, δ (ppm): 1.5 1.7 (m, 3H), 1.80–2.0 (m, 1H), 2.17 (m, 1H), 2.35 (s, 3H), 2.55–2.60 (m, 1H), 2.98 (m, 1H), 3.14 (m, 1H), 3.40(m, 1H), 6.50(d, J=5 Hz, 1H), 7.21 (t, J=6 Hz, 1H), 7.45 (dd, J=2.5 Hz und 9.5 Hz, 1H), 7.79 (d, J=2.5 Hz, 1H), 8.24 (d, J=5 Hz, 1H), 8.40 (d, J=9.5 Hz, 1H).

Example 13

(7-Chloro-quinolin-4-yl)-(1,1-dimethyl-2-pyrrolidin-1-yl-ethyl)-amine 4.95 g of 4,7-dichloroquinoline, 7.1 g of 2-methyl-2-(pyrrolidin-1-yl)-propylamine and 5 g of phenol were reacted at 140° C. for 16 hours. After cooling, 25 ml of water were added, the mixture was adjusted to pH 1 with a small amount of concentrated hydrochloric acid so and extracted three times with 50 ml of ethyl acetate each time. Thereafter, concentrated sodium hydroxide solution was added to pH 12 and the product was extracted three times with 100 ml of ethyl acetate each time. The crude product obtained after evaporation of the solvent was purified by chromatography on 400 g of aluminium oxide (activity grade II) with a mixture of ethyl acetate and hexane (1:4). 2.37 g of colourless crystals, m.p.: 89°–91° C., were obtained after recrystallization from hexane.

$^1$H-NMR in CDCl$_3$, δ (ppm): 1.48 (s, 6H), 1.86 (m, 4H), 2.71(s, 2H), 2.75 (m, 4H), 6.60 (d, J=6 Hz, 1H), 6.84 (br., 1H), 7.33 (dd, J=3 Hz and 9 Hz, 1H), 7.62 (d, J=9 Hz, 1H), 7.91 (d, J=3 Hz, 1H), 8.45 (d, J=6 Hz, 1H).

The dihydrochloride was obtained by adding 3.3N HCl in dioxan to a solution of the base in anhydrous dioxan; colourless crystals, m.p.: 249°–252° C.

Example 14

(7-Chloro-quinolin-4-yl)-(1,1-dimethyl-2-piperidin-1-yl-ethyl)-amine 4.57 g of 4,7-dichloroquinoline, 7.5 g of 2-methyl-2-(piperidin-1-yl)-propylamine and 0.75 g of phenol were reacted at 180° C. for 16 hours. The crude reaction product, isolated as in the preceeding Example, was purified on 200 g of aluminium oxide (activity grade II) prior to recrystallization; a 1:1 mixture of toluene and acetone was used as the eluent. After a fore-run, which contained unreacted 4,7-dichloroquinoline, the product was eluted and, after recrystallization from 5 ml of acetonitrile, yielded 0.8 g of colourless crystals, m.p.: 143°–147° C.

$^1$H-NMR in CDCl$_3$, δ (ppm): 1.46 (s, 6H), 1.50 (m, 2H), 1.65 (m, 4H), 2.51 (s, 2H), 2.65 (m, 4H), 6.62 (d, J=6 Hz, 1H), 6.83 (br.s, 1H), 7.37 (dd, J=3 Hz and 9 Hz, 1H), 7.71 (d, J=9 Hz, 1H), 7.93 (d, J=3 Hz, 1H), 8.46 (d, J=6 Hz, 1H).

Example 15

N$_3$-(7-Chloro-quinolin-4-yl)-N$_1$,N$_1$-dimethyl-propane-1,3-diamine

From 4,7-dichloroquinoline and 3-(N,N-dimethylamino)-propylamine; colourless crystals from ethyl acetate-hexane, m.p.: 111°–113° C.

$^1$H-NMR in CDCl$_3$, δ (ppm): 1.86 (quintet, J=6 Hz, 2H), 2.37 (s, 6H), 2.58 (m, 2H), 3.39 (m, 2H), 6.31 (d, J=5.5 Hz, 1H), 7.32 (dd, J=2 Hz and 9 Hz, 1H), 7.58 (d, J=9 Hz, 1H), 7.92 (d, J=2 Hz, 1H), 7.94 (br.s, 1H). 8.48 (d, J=5.5 Hz ).

Example 16

N$_3$-(7-Chloro-quinolin-4-yl)-N$_1$,N$_1$-diethyl-propane-1,3-diamine 2.99 g of base from 3.96 g of 4,7-dichloroquinoline and 5.2 g of 3-(N,N-diethylamino)-propylamine (reaction duration 4 hours at 140° C.); colourless crystals from acetonitrile, m.p.: 77°–78° C.

$^1$H-NMR in CDCl$_3$, δ (ppm): 1.10 (t, J=7 Hz, 6H), 1.92 (quintet, J=6 Hz, 2H), 2.65 (m, 6H), 3.38 (m, 2H), 6.29 (d, J=5.5 Hz, 1H), 7.32 (dd, J=2.5 Hz and 9 Hz, 1H), 7.68 (d, J=9 Hz, 1H), 7.92 (d J=2.5 Hz, 1H), 8.18 (br.s, 1H). 8.50 (d, J=5.5 Hz).

The dihydrochloride was obtained with isopropanolic hydrochloric acid; colourless crystals from isopropanol, decomposition starting at 118° C.

Example 17

(7-Chloro-quinolin-4-yl)-(3-pyrrolidin-1-yl-propyl)-amine 3.08 g from 7.72 g of 4,7-dichloroquinoline and 5 g of 3-(pyrrolidin-1-yl)-propylamine (reaction duration 16 hours at 140° C.); the base was converted with isopropanolic hydrochloric acid into the dihydrochloride which when recrystallized from acetonitrile/ethanol, yielded colourless crystals, m.p.: 204°–206° C.

$^1$H-NMR in DMSO-d$_6$; δ (ppm): 1.96 (m, 4H), 2.14 (m, 2H), 3.00 (m, 2H), 3.26 (m, 2H), 3.51 (m, 2H), 3.67 (m, 2H), 6.96 (d, J=7 Hz, 1H), 7.78 (dd, J=2.5 Hz and 9 Hz, 1H), 8.13 (d, J=2.5 Hz, 1H), 8.59 (d, J=7 Hz, 1H), 8.81 (d, J=9 Hz, 1H), 9.86 (d, J=6 Hz, 1H), 11.13 (br.s, 1H). 14.55 (br.s, 1H).

Example 18

(7-Chloro-quinolin-4-yl)-(3-piperidin-1-yl-propyl)-amine 2.73 g from 2.83 g of 3-(piperidin-1-yl)-propylamine and 3.94 g of 4,7-dichloroquinoline (reaction duration, 16 hours at 140° C.); the base (yellowish crystals from acetonitrile, m.p.: 113°–116° C.) was converted with isopropanolic hydrochloric acid into the dihydrochloride which when recrystallized from acetonitrile/ethanol, yielded colourless crystals, m.p.: 137°–141° C.

$^1$H-NMR in DMSO-d$_6$; δ (ppm): 1.28 (m, 1H), 1.54–1.76 (m, 5H), 2.08 (m, 2H), 2.78 (m, 2H), 3.07 (m, 2H), 3.27–3.38 (m, 2H), 3.53 (m, 2H), 6.21 (d, J=7 Hz, 1H), 7.55 (dd, J=2.5 Hz and 9 Hz, 1H), 8.01 (d, J=2.5 Hz, 1H), 8.43 (d, J=7 Hz, 1H), 8.73 (d, J=9 Hz, 1H), 9.88 (d, J=6 Hz, 1H), 10.67 (br.s, 1H). 14.63 (br.s, 1H).

Example 19

(1-Benzyl-piperidin-4-yl)-(7-chloro-quinolin-4-yl)-amine 5.65 g from 10 g of 4,7-dichloroquinoline and 10.26 ml of 4-amino-1-benzylpiperidine; colourless crystals from acetonitrile, m.p.: 166°–168° C. The dihydrochloride, colourless crystals from acetonitrile/ethanol, m.p. above 25° C., was obtained therefrom using isopropanolic hydrochloric acid.

$^1$H-NMR in DMSO-d$_6$; δ (ppm): 2.1–2.4 (m, 4H), 3.04 (m, 2H), 3.44 (m, 2H), 4.08 (br.s, 1H), 4.30 (s, 2H), 7.04 (d, J=7.5 Hz, 1H), 7.48 (m, 3H), 7.67 (m, 2H), 7.78 (dd, J=2.5 Hz and 9 Hz, 1H), 8.12 (d, J=2.5 Hz, 1H), 8.61 (d, J=7.5 Hz, 1H), 8.81 (d, J=9.5 Hz, 1H), 9.30 (d, J=6 Hz, 1H), 11.50 (br.s, 1H). 14.55 (br.s, 1H).

Example 19a

(RS)-(7-Chloro-quinolin-4-yl)-(1-methyl-piperidin-3-yl)-amine 4 g from 11.29 g of 4,7-dichloroquinoline and 6.5 g of 3-amino-1-methyl-piperidine; colourless crystals from acetonitrile, m.p.: 149°–150° C.

C$_{15}$H$_{18}$ClN$_3$ (275.78):

Calc.: C 65.33%, H 6.58%, Cl 12.86%, N 15.24% Found: C 65.25%, H 6.64%, Cl 12.87%, N 15.11%

$^1$H-NMR in DMSO-d$_6$; δ (ppm): 1.3–1.95 (multiple m, 6H), 2.02 (s, 3H), 2.67 (m, 1H), 2.92 (m, 1H), 3.67 (m, 1H), 6.54 (d, J=6 Hz, 1H), 6.83 (d, J=8 Hz, 1H), 7.44 (dd, J=2.5 Hz and 9 Hz, 1H), 7.78 (d, J=2.5 Hz, 1H), 8.32 (d, J=9 Hz, 1H), 8.39 (d, J=6 Hz, 1H).

Example 20

(5-Amino-2,2,4-trimethyl-cyclopentylmethyl)-(7-chloro-quinolin-4yl)-amine 480 mg as a mixture of isomers from 3.1 g of 4-bromo-7-chloroquinoline and 11 ml of 2-(aminomethyl)-3,3,5-trimethyl-cyclopentylamine; colourless crystals from isopropanolic hydrochloric acid, m.p. above 250° C. The $^1$H-NMR (250 Mz) shows the presence of a mixture of two main components and two secondary components.

C$_{18}$H$_{24}$N$_3$Cl.2HCl.0.5 H$_2$O:

Calculated: C: 54.08%, H: 6.81%, N: 10.51%, Cl: 26.60%
Found: C: 54.24%, H: 6.82%, N: 10.76%, Cl 26.71%

Example 21

N$_1$,N$_1$-Diethyl-N$_2$-(7-trifluoromethyl-quinolin-4-yl)-ethane-1,2-diamine 5 g of 4-chloro-7-(trifluoromethyl)-quinoline and 10 g of 2-N,N-diethylamino-ethylamine in 150 ml of dimethylacetamide were stirred at 120° C. for 16 hours. After cooling, the mixture was concentrated in a water-jet vacuum and the residue was taken up with 150 ml of water and a small amount of hydrochloric acid such that the pH amounts to 4.8. After three-fold extraction with 100 ml of ethyl acetate each time, the mixture was adjusted to pH 10.2 by means of 1N sodium hydroxide solution and the basic product was extracted with 3×100 ml of ethyl acetate. After evaporation of the solvent the product was recrystallized from acetonitrile and there were obtained 1.96 g of colourless crystals, m.p.: 122°–124° C.

$^1$H-NMR in CDCl$_3$; δ (ppm): 1.08 (t, J=7 Hz, 6H), 2.61 (q, J=7 Hz, 4H), 2.83 (t, J=6 Hz, 2H), 3.27 (m, 2H), 6.23 (m, 1H), 6.45 (d, J=6 Hz, 1H), 7.60 (dd, J=3 Hz and 9 Hz, 1H), 7.85 (d, J=9 Hz, 1H), 8.26 (m, 1H), 8.61 (d, J=6 Hz, 1H).

In a manner analogous to Example 21, we prepared the following compounds:

Example 22

N$_1$,N$_1$-Dimethyl-N$_2$-(7trifluoromethyl-quinolin-4-yl)-ethane-1,2-diamine From 4-chloro-7-(trifluoromethyl)-quinoline and 2-N,N-dimethylamino-ethylamine; colourless crystals from hexane, m.p.: 110°–113° C. $^1$H-NMR in CDCl$_3$; δ (ppm): 2.31 (s, 6H), 2.69 (m, 2H), 3.29 (m, 2H), 6.05 (m, 1H), 6.44 (d, J=6 Hz, 1H), 7.51 (dd, J=3 Hz and 9 Hz, 1H), 7.90 (d, J=9 Hz, 1H), 8.26 (m, 1H), 8.61 (d, J=6 Hz, 1H).

Example 23

(RS)-(7-Chloro-quinolin-4-yl)-[2-(3-methyl-piperidin-1-yl)-ethyl]-amine 2.5 g of N-(2-chloroethyl)-7-chloro-4-quinolinamine hydrochloride in 25 ml of 3-methylpiperidine were held at 100° C. in a sealed tube for 24 hours. Thereafter, 100 ml of water were added, the mixture is adjusted to pH 12 by means of concentrated sodium hydroxide solution and extracted three times with 50 ml of ethyl acetate each time. The combined extracts were washed with a small amount of water and concentrated. The residue was recrystallized from 80 ml of acetone. 0.88 g of colourless crystals, m.p.: 148°–151° C., was obtained.

$^1$H-NMR in CDCl$_3$; δ (ppm): 0.90 (d, J=6 Hz, 3H), 0.98 (m, 1H), 1.6–1.75 (m, 5H), 2.04 (dt, J=3.5 Hz and 7 Hz, 1H), 2.75 (m, 2H), 2.84 (m,2H), 3.31 (m, 2H), 6.20 (broad, 1H), 6.37 (d, J=6 Hz, 1H), 7.38 (dd, J=3 Hz and 9 Hz, 1H), 7.70 (d, J=9 Hz, 1H), 7.96 (d, J=3 Hz, 1H), 8.53 (d, J=6 Hz, 1H).

The following compounds were prepared in a manner analogous to Example 23:

Example 24

(7-Chloro-quinolin-4-yl)-[2-(4-methyl-piperidin-1-yl)-ethyl]-amine 2.72 g from 2.5 g of N-(2-chloroethyl)-7-chloro-4-quinolinamine hydrochloride; colourless crystals from acetonitrile, m.p.: 154°–156° C.

$^1$H-NMR in CDCl$_3$; δ (ppm): 0.96 (d, J=6 Hz, 3H), 1.28 (m, 2H), 1.43 (m, 1H), 1.68 (m, 1H), 2.06 (m, 2H), 2.73 (m, 2H), 2.90 (m,2H), 3.29 (m, 2H), 6.10 (broad, 1H), 6.36 (d, J=6 Hz, 1H), 7.36 (dd, J=3 Hz and 9 Hz, 1H), 7.68 (d, J=9 Hz, 1H), 7.95 (d, J=3 Hz, 1H), 8.52 (d, J=6 Hz, 1H).

Example 25

(7-Chloro-quinolin-4-yl)-[2-(3,3-dimethyl-piperidin-1-yl)-ethyl]-amine 2.1 g from 2.5 g of N-(2-chloroethyl)-7-chloro-4-quinolinamine hydrochloride; colourless crystals from acetonitrile, m.p.: 151°–153° C.

$^1$H-NMR in CDCl$_3$; δ (ppm): 0.98 (s, 6H), 1.29 (m, 2H), 1.66 (m, 1H), 2.12 (m, 2H), 2.45 (m, 2H), 2.69 (t, J=6 Hz, 2H), 3.28 (m, 2H), 6.20 (broad, 1H), 6.36 (d, J=6 Hz, 1H), 7.37 (dd, J=3 Hz and 9 Hz, 1H), 7.68 (d, J=9 Hz, 1H), 7.96 (d, J=3 Hz, 1H), 8.52 (d, J=6 Hz, 1H).

Example 26

(RS)-(7-Chloro-quinolin-4-yl)-[2-(2-methyl-piperidin-1-yl)-ethyl]-amine 1.4 g from 2.5 g of N-(2-chloroethyl)-7-chloro-4-quinolinamine hydrochloride; colourless crystals from acetonitrile, m.p.: 133°–134° C.

$^1$H-NMR in CDCl$_3$; δ (ppm): 1.12 (d, J=6.5 Hz,6H), 1.30–1.75 (m, 6H), 2.17 (dt, J=4 Hz and 10 Hz, 2H), 2.45–2.55 (m, 2H), 2.86 (tm, 1H), 3.1–3.3 (m, 3H), 6.13 (broad, 1H), 6.36 (d, J=6 Hz, 1H), 7.38 (dd, J=3 Hz and 9 Hz, 1H), 7.67 (d, J=9 Hz, 1H), 7.95 (d, J=3 Hz, 1H), 8.52 (d, J=6 Hz, 1H).

Example 27

(RS)-(7-Chloro-quinolin-4-yl)-[2-(2-ethyl-piperidin-1-yl)-ethyl]amine 1.52 g from N-(2-chloroethyl)-7-chloro-4-quinolinamine hydrochloride; colourless crystals from acetonitrile, m.p.: 115°–117° C.

$^1$H-NMR in CDCl$_3$; δ (ppm): 0.93 (t, J=7.5 Hz, 3H), 1.3–1.75 (m, 8H), 2.21 (m, 2H), 2.39 (m, 2H), 2.57 (m, 1H), 2.85 (m, 1H), 3.16 (m, 1H), 3.26 (m, 2H), 5.17 (broad 1H), 6.36 (d, J=6 Hz, 1H), 7.37 (dd, J=3 Hz and 9 Hz, 1H), 7.65 (d, J=9 Hz, 1H), 7.95 (d, J=3 Hz, 1H), 8.52 (d, J=6 Hz, 1H).

Example 28

(2R,6S)-(7-Chloro-quinolin-4-yl)-[2-(2,6-dimethyl-piperidin-1-yl)-ethyl]-amine 0.4 g from 2.5 g of N-(2-chloroethyl)-7-chloro-4-quinolinamine hydrochloride; colourless crystals from acetonitrile, m.p.: 138°–139° C.

$^1$H-NMR in CDCl$_3$; δ (ppm): 1.14 (d, J=6.5 Hz, 6H), 1.2–1.7 (m, 6H), 2.57 (m, 2H), 2.94 (t, J=7 Hz, 2H), 3.31 (m, 2H), 5.85 (broad, 1H), 6.38 (d, J=6 Hz, 1H), 7.37 (dd, J=2.5 Hz and 9.5 Hz, 1H), 7.70 (d, J=9.5 Hz, 1H), 7.95 (d, J=2.5 Hz, 1H), 8.53 (d, J=6 Hz, 1H).

Example 29

(7-Chloro-quinolin-4-yl)-[2-(3,5-dimethyl-piperidin-1-yl)-ethyl]-amine 0.67 g (isomer mixture cis:trans=3:1) from 2.5 g of N-(2-chloroethyl)-7-chloro-4-quinolinamine hydrochloride; colourless crystals from acetonitrile, m.p.: 142°–143° C.

$^1$H-NMR in CDCl$_3$; δ (ppm): 0.88 and 1.00(d, J=6.5 Hz, 6H; ratio 3:1), 1.3–2.0 (several m, 4H), 2.2–2.84 (several m, 6H), 3.29 (m, 2H), 6.12 and 6.20 (broad, 1H; ratio 3:1), 6.37 (d, J=6 Hz, 1H), 7.37 (dd, J=3 Hz and 9 Hz, 1H), 7.66 (d, J=9 Hz, 1H), 7.95 (d, J=3 Hz, 1H), 8.53 (d, J=6 Hz, 1H).

Example 30

(7-Chloro-quinolin-4-yl)-[2-(2,5-dimethyl-pyrrolidin-1-yl)-ethyl]-amine 0.35 g (isomer mixture cis:trans=15:1) from 1.3 g of N-(2-chloroethyl)-7-chloro-4-quinolinamine hydrochloride; yellowish crystals from acetone, m.p.: 127°–130° C.

$^1$H-NMR in DMSO-D$_6$; δ (ppm): 0.94 and 1.06(d, J=6.5 Hz, 6H; ratio 15:1), 1.29 (m, 2H), 1.80 (m, 2H), 2.67 (m, 2H), 2.79 (m, 2H), 3.34 (m, 2H),), 6.47 (d, J=6 Hz, 1H), 7.05 (br.t, 1H), 7.46 (dd, J=3 Hz and 9 Hz, 1H), 7.78 (d, J=3 Hz, 1H), 8.19 (d, J=9 Hz, 1H), 8.40 (d, J=6 Hz, 1H).

Example 31

(7-Chloro-quinolin-4-yl)-[2-octahydro-indol-1-yl)-ethyl]-amine 0.3 g from 2.2 g of N-(2-chloroethyl)-7-chloro-4-quinolinamine hydrochloride; colourless crystals from ethyl acetate, m.p.: 115°–117° C.

$^1$H-NMR in DMSO-d$_6$; δ (ppm): 1.1–2.0 (m, 11H), 2.15–2.45 (m, 2H), 2.95 (m, 1H), 3.18 (m, 1H), 3.36 (m, 4H), 6.48 (d, J=6 Hz, 1H), 7.22 (t, J=6 Hz, 1H), 7.45 (dd, J=3

Hz and 9 Hz, 1H), 7.91 (d, J=3 Hz, 1H), 8.19 (d, J=9 Hz, 1H), 8.40 (d, J=6 Hz, 1H).

Example 32

2-(3-Azabicyclo[3.2.2]nonan-3-yl)-ethyl]-(7-chloro-quinolin-4-yl)-amine 0.45 g from 1.48 g of N-(2-chloroethyl)-7-chloro-4-quinolinamine hydrochloride; yellowish crystals from ethanol, m.p.: 205°–207° C.

$^1$H-NMR in CDCl$_3$; δ (ppm): 1.60–1.82 (m, 8H), 1.95 (br.s, 2H), 2.66 (d, J=4.5 Hz, 4H), 2.81 (m, 2H), 3.27 (m, 2H), 6.30 (broad, 1H), 6.36 (d, J=6 Hz, 1H), 7.39 (dd, J=3 Hz and 9 Hz, 1H), 7.69 (d, J=9 Hz, 1H), 7.95 (d, J=3 Hz, 1H), 8.53 (d, J=6 Hz, 1H).

Example 33

N$_1$-Allyl-N$_2$-(7-chloro-quinolin-4-yl)-N$_1$-methyl-ethane-1,2-diamine 0.56 g from 2.5 g of N-(2-chloroethyl)-7-chloro-4-quinolinamine hydrochloride; colourless crystals from acetonitrile, m.p.: 91°–93° C.

$^1$H-NMR in DMSO-d$_6$; δ (ppm): 2.24 (s,3H),), 2.62 (t, J=7 Hz, 2H), 3.04 (d, J=7 Hz, 2H), 3.37 (m, 2H), 5.1–5.2 (m, 2H), 5.84 (m, 1H), 6.49 (d, J=6 Hz, 1H), 7.21 (t, J=6 Hz, 1H), 7.45 (dd, J=3 Hz and 9 Hz, 1H), 7.78 (d, J=3 Hz, 1H), 8.22 (d, J=9 Hz, 1H), 8.40 (d, J=6 Hz, 1H).

Example 33a (R,S)-(7-Chloro-quinolin-4-yl)-(1-methyl-pyrrolidin-3-yl)-amine 0.42 g of (R,S)-(7-chloro-quinolin-4-yl)-(pyrrolidin-3-yl)-amine dihydrobromide was boiled under reflux overnight in 2 ml of formic acid and 2 ml of 37% formalin solution. Thereafter, 10 ml of water were added, the mixture was adjusted to pH 2 with conc. hydrochloric acid and extracted three times with 20 ml of ethyl acetate each time. Thereafter, the aqueous phase was adjusted to pH 12 by the addition of conc. sodium hydroxide solution and extracted three times with 20 ml of ethyl acetate each time. After evaporation of the solvent the residue was recrystallized from tert.-butyl methyl ether and acetone yielding 20 mg of colourless crystals, m.p.: 150°–152° C.

$^1$H-NMR in DMSO-d$_6$; δ (ppm): 1.75–2 (m, 1H), 2.29 (s,3H), 2.3–2.8 (multiple m, 5H), 4.13 (m, 1H), 6.47 (d, J=6 Hz, 1H), 7.29 (d, J=6.5 Hz, 1H), 7.45 (dd, J=3 Hz and 9 Hz, 1H), 7.78 (d, J=3 Hz, 1H), 8.39 (d, J=6 Hz, 1H), 8.40 (d, J=9 Hz, 1H).

Example 33b

N$_1$-(7-Chloro-quinolin-4-yl)-2,N$_2$,N$_2$-trimethyl-propane-1,2-diamine 30 g of N$_1$-(7-chloro-quinolin-4-yl)-2-methyl-propane-1,2-diamine were boiled under reflux for 3 hours in 21.6 ml of aqueous formaldehyde solution (37%) and 45.3 ml of formic acid. Thereafter, the mixture was evaporated to dryness in a vacuum and the residue was taken up in 100 ml of water and adjusted to pH 12 using conc. potassium hydroxide solution. The precipitated product was recrystallized from 250 ml of acetonitrile yielding 25.1 g, m.p.: 114°–116° C.

C$_{11}$H$_{20}$ClN$_3$ (277.80):

Calc.: C 64.85%, H 7.26%, Cl 12.76%, N 15.13% Found: C 64.64%, H 7.18%, Cl 12.79%, N 15.07%

$^1$H-NMR in DMSO-d$_6$; δ (ppm): 1.09 (s, 6H), 2.22 (s, 6H), 3.18 (d, J=5.5 Hz, 2H), 6.46 (t, J=5.5 Hz, 1H), 6.51 (d, J=6 Hz, 1H), 7.48 (dd, J=2 Hz and 9.5 Hz, 1H), 7.82 (d, J=2.5 Hz, 1H), 8.07 (d, J=9.5 Hz, 1H), 8.42 (d, J=6 Hz, 1H).

Example 33c (S)-N$_2$-(7-Chloro-quinolin-4-yl)-N$_1$,N$_1$-dimethyl-propane-1,2-diamine 19 g of (S)-2-amino-1-chloro-N-(7-chloro-quinolin-4-yl)-propane hydrochloride were dissolved in 190 ml of dimethylamine solution (33% in ethanol) and held at 110° C. in an autoclave for 15 hrs. After cooling and evaporation the residue was dissolved in 200 ml of dichloromethane and extracted with 200 ml of 1N NaOH. The basic aqueous phase was back-extracted with 200 ml of dichloromethane. The dichloromethane phases were dried and evaporated. The crude product was chromatographed on neutral aluminium oxide (act. II) in hexane/ethyl acetate 2:1, then in ethyl acetate alone. The resulting oil was triturated with 100 ml of diethyl ether and, after crystallization had taken place, diluted with 50 ml of hexane. We obtained 13.5 g (79%) of white crystals; m.p. 110° C., [a]$_D$=+115° (c=1.0, MeOH).

For the preparation of the dihydrochloride, 19.8 g of free base were dissolved in 200 ml of acetone, cooled in ice and then treated with 75 ml of 2N HCl and stirred for 10 min. After evaporation the residue was treated with 200 ml of toluene and again evaporated. The resulting oil was dissolved in 200 ml of ethanol while warming, filtered and, after crystallization had taken place, diluted with 50 ml of diethyl ether yielding 23.7 g (94%) of white crystals; m.p.: >260° C., [a]$_D$=+136.5° (c=1.0, MeOH).

$^1$H-NMR (250 MHz) in d$_6$-DMSO, signals at δ (ppm): 1.31 (d, J=6.3, 3H), 2.81 (s, 6H), 3.39 (dd, 1H), 4.00 (dd, 1H), 4.73 (m, 1H), 7.08 (d, J= 7, 1H), 7.75 (dd, J$_1$=9, J$_2$=2, 1H), 8.15 (d, J=2, 1H), 8.65 (d, J=7, 1H), 9.06 (d, J=9, 1H), 9.67 (d, J=9, 1H), 10.5 (br, 1H), 15.0 (br, 1H)

Example 33d (R)-N$_2$-(7-Chloro-quinolin-4-yl)-N$_1$,N$_1$-dimethyl-propane-1,2-diamine Analogously to Example 33c, starting from (R)-2-amino-1-chloro-N-(7-chloro-quinolin-4-yl)-propane hydrochloride there is prepared (R)-N$_1$-(7-chloro-quinolin-4-yl)-N$_2$,N$_2$-dimethyl-propane-1,2-diamine hydrochloride; white crystals; m.p.: >260° C., [a]$_D$=−132° (c=1.0, MeOH).

Example 33e (S)-N$_2$-(7-Chloro-quinolin-4-yl)-N$_1$, N$_1$-diethyl-propane-1,2-diamine 15 g of (S)-2-amino-1-chloro-quinolin-4-yl)-propane hydrochloride were dissolved in 100 ml of methanol and 50 ml of diethylamine and held at 125° C. in an autoclave for 15 hrs. After cooling and evaporation, the residue was dissolved in 200 ml of dichloromethane and extracted with 200 ml of 1N NaOH. The basic aqueous phase was back-extracted with 200 ml of dichloromethane. The dichloromethane phases were dried and evaporated. The crude product was chromatographed on neutral aluminium oxide (act. II) in hexane/ethyl acetate 2:1. The resulting oil was dissolved in 40 ml of diethyl ether and diluted slowly with 200 ml of hexane yielding 10.3 g (69%) of white crystals; m.p.: 89° C., [a]$_D$=+122.6° (c=1.0, MeOH).

For the preparation of the dihydrochloride, 18.1 g of free base were dissolved in 190 ml of acetone, cooled in ice and then treated with 62.5 ml of 2N HCl and stirred for 10 min. After evaporation the residue was treated with 200 ml of toluene and again evaporated. The resulting oil was dissolved in 200 ml of ethanol while warming, filtered, concentrated to 100 ml and, for crystallization, diluted with 2× 50 ml of diethyl ether yielding 21.8 g (96%) of white crystals; m.p.: 165°–170° C., [a]$_D$=+150.6° (c=1.0, MeOH).

$^1$H-NMR (250 MHz) in d$_6$-DMSO, signals at δ (ppm): 1.26 (t, J=7, 6H), 1.36 (d, J=6.3, 3H), 3.17 (q, J=7, 4H), 3.35 (dd, 1H), 4.01 (dd, 1H), 4.72 (m, 1H), 7.10 (d, J=7, 1H), 7.75 (dd, J$_1$=9, J$_2$=2, 1H), 8.17 (d, J=2, 1H), 8.65 (d, J=7, 1H), 9.08 (d, J=9, 1H), 9.81 (d, J=9, 1H), 10.5 (br, 1H), 15.0 (br, 1H)

Example 33f (R)-N$_2$(7-Chloro-quinolin-4-yl)-N$_1$, N$_1$-diethyl-propane-1,2-diamine Analogous to Example 33e, starting from (R)-2-amino-1-chloro-N$_1$-(7-chloro-quinolin-4-yl)-propane hydrochloride, we prepared (R)-N$_1$-(7-chloro-quinolin-4-yl)-N$_2$,N$_2$-dimethyl-propane-1,2-diamine hydrochloride; white crystals, mp.: 165°–170° C., [a]$_D$=−140.3° (c=1.0, MeOH).

Example 33g 2.2 g of (S)-N$_2$,N$_2$-dimethyl-1,2-propanediamine and 2 g of 4,7-dichloroquinoline in 4 ml of 1-methyl-2-pyrrolidone were held at 150° C. in an autoclave for 6.5 hrs. After cooling, the reaction mixture was poured into 20 ml of 3N HCl and extracted with 4×20 ml of dichloromethane. The acidic-aqueous phase was made basic with 28% NaOH and then extracted with 3×20 ml of dichloromethane. The crude product was chromatographed on neutral aluminium oxide (act. II) in hexane/ethyl acetate 10:3, yielding 1.25 g of yellow oil. This oil was dissolved in 10 ml of ethanol and converted into the dihydrochloride with ethanolic HCl solution, yielding 450 mg of white crystals; m.p.: 165° C., [a]$_D$=+15.1° (c=1.0, MeOH).

$^1$H-NMR (250 MHz) in d$_6$-DMSO, signals at δ (ppm): 1.34 (d J=6.1, 3H), 2.79 (s, 6H), 3.80 (m, 2H), 4.01 (m, 1H), 7.16 (d, J=7, 1H), 7.78 (dd, J$_1$=9, J$_2$=2, 1H), 8.17 (d, J=2, 1H), 8.65 (d, J=7, 1H), 8.93 (d, J=9, 1H), 9.92 (br, 1H), 11.1 (br, 1H), 15.0 (br, 1H)

Example 33h (R)-N$_1$-(7-Chloro-quinolin-4-yl)-N$_2$,N$_2$-dimethyl-propane-1,2-diamine Analogous to Example 33g, starting from (R)-N$_2$,N$_2$-dimethyl-1,2-propanediamine hydrochloride, we prepared (R)-N$_1$-(7-chloro-quinolin-4-yl)-N$_2$,N$_2$-dimethyl-propane-1,2-diamine hydrochloride; white crystals, m.p.: 250° C., [a]$_D$=−9.4° (c=1.0, MeOH).

C$_{14}$H$_{19}$Cl$_3$N$_3$ (336.69):
Calc.: C 49.94%, H 5.99%, Cl 31.59%, N 12.48% Found: C 49.69%, H 6.18%, Cl 31.85%, N 12.28%
The Intermediates Used Herein Were Prepared as Follows:

Example 34

(7-Chloro-quinolin-4-yl)-(2-chloro-ethyl)-amine 20 ml of thionyl chloride were slowly added dropwise while stirring to a suspension of 12.3 g of 2-(7-chloro-quinolin-4-amino)-ethanol [prepared according to R. C. Elderfield et al., J. Am. Chem. Soc. 68, 1250 (1946)] in such a manner that the temperature could be held at about 30° C. without external cooling. The mixture was stirred at RT for one hour and thereafter evaporated to dryness. The residue was crystallized from 120 ml of glacial acetic acid yielding colourless crystals which, after suspension in 250 ml of toluene, were dried at 50° C. under a water-jet vacuum. 9.75 g of colourless crystalline product, m.p. 239°–240° C., were obtained.

$^1$H-NMR in CDCl$_3$; δ (ppm): 3.97 (s, 4H), 7.02 (d, J=8 Hz, 1H), 7.80 (dd, J=3 Hz and 9 Hz, 1H), 8.14 (d, J=3 Hz, 1H), 8.60 (d, J=8 Hz, 1H), 8.75 (d, J=9 Hz, 1H), 9.85 (br.s, 1H), 14.63 (br.s, 1H).

Example 35

4-Bromo-7-chloro-quinoline 83.9 g of 7-chloro-4-hydroxyquinoline were added portionwise at 60° to 150 g of phosphorus oxybromide and the mixture was thereafter heated to 140° C. for 6 hours. After cooling, the mixture was treated with 3 l of ice-water and extracted with 2×1.5 l of dichloromethane. After evaporation of the solvent and crystallization from 1.3 l of hexane, 34 g of product were obtained as colourless crystals, m.p.: 102°–103° C.

Example 36

1-Methyl-2-pyrrolidin-1-yl-ethylamine 15 ml of aqueous formaldehyde solution (37%) were added dropwise at 5° C. within one hour to 16.5 ml of pyrrolidine. Thereafter, 57.2 ml of nitroethane were added and the mixture was stirred at RT overnight. 150 ml of ethyl acetate and 400 ml of saturated sodium chloride solution were added, the organic phase was separated and subsequently distilled in a water-jet vacuum. The product, 1-(2-nitropropyl)-pyrrolidine (18.5 g) was collected at 85°–87° C.

13.1 g of this intermediate were then hydrogenated in 100 ml of methanol under 100 bar and at 80° C. after the addition of 0.65 g of Raney-nickel. The product, 1-methyl-2-pyrrolidin-1-yl-ethylamine, was obtained by distillation at 49°–52° C. in a water-jet vacuum (4.7 g; colourless liquid).

The following diamines were prepared in an analogous manner to Example 36 by using the corresponding amines:
1-Methyl-2-piperidin-1-yl-ethylamine;
N,N-diethyl-propane-1,2-diamine;
N,N-dimethyl-propane-1,2-diamine.

Example 37

N,N-Diethyl-cyclohexane-1,2-diamine 30 g of cyclohexene oxide were reacted with 44.8 g of diethylamine and 32.6 g of lithium perchlorate in 300 ml of acetonitrile overnight while stirring and under reflux. Thereafter, 200 ml of water were added and the product was extracted with 3×150 ml of ethyl acetate. After evaporation of the solvent, 30.4 g of 2-(diethylamino)-cyclohexanol remained. This was dissolved in 150 ml of tetrahydrofuran without further purification. After the addition of 38.6 g of phthalimide and 68.7 g of triphenylphosphine 45.9 g of diethyl azodicarboxylate were added dropwise at a temperature of 10°–15° C. and the mixture was stirred at RT overnight. Thereafter, the mixture was evaporated, the residue was suspended in dilute hydrochloric acid (200 ml, pH 1) and washed with 3×150 ml of ethyl acetate. The pH was then adjusted to 12–13 by adding concentrated sodium hydroxide solution and the intermediate was extracted using 3×200 ml of ethyl acetate. After evaporation of the solvent, 36.8 g of N,N-diethyl-2-phthalimido-cyclohexylamine were obtained in the form of yellow crystals.

The yellow crystals were saponified overnight in 250 ml of concentrated hydrochloric acid under reflux. After threefold washing using 200 ml of dichloromethane each time, the pH was adjusted to 13–14 by adding concentrated sodium hydroxide solution and the product was extracted using 3×200 ml of ethyl acetate. After evaporation of the solvent, we obtained as a yellowish oil, 13.4 g of N,N-diethyl-cyclohexane-1,2-diamine, which was processed without further purification.

2-Pyrrolidin-1-yl-cyclohexylamine is prepared in an analogous manner using pyrrolidine in place of diethylamine.

Similarly, in an analogous manner to Example 37 above, we obtained N,N-diethyl-cyclopentane-1,2-diamine from cyclopentene oxide and diethylamine, as well as 2-pyrrolidin-1-yl-cyclopentylamine from cyclopentene oxide and pyrrolidine.

Example 38

1,1-Dimethyl-2-pyrrolidin-1-yl-ethylamine 18 ml of 2-nitropropane and 16.5 ml of pyrrolidine were dissolved in 60 ml of dioxan. 15 ml of aqueous formaldehyde solution (37%) and 8 ml of 2% sodium hydroxide solution were added at 5° C. The mixture was heated to 90° C. while stirring for 1 hour, cooled and thereafter extracted with 3×150 ml of ethyl acetate. Upon distillation in a water-jet vacuum, we obtained 19 g of 1-(2-nitro-2-methylpropyl)-pyrrolidine.

This intermediate was then hydrogenated in 100 ml of methanol under 100 bar and at 80° C. after the addition of 1.5 g of Raney-nickel. The product, 1,1-dimethyl-2-pyrrolidin-1-yl-ethylamine, was obtained by distillation in a water-jet vacuum at 52°–57° C. (13.1 g; colourless liquid).

1,1-Dimethyl-2-piperidin-1-yl-ethylamine is prepared in an analogous manner using piperidine in place of pyrrolidine.

Example 39

3-Piperidin-1-yl-propylamine 3.7 g of piperidine and 2.3 g of acrylonitrile were pooled and heated to 100° C. for 3 hours. After cooling, the mixture was taken up in 40 ml of isopropanol and the 3-(1-piperidino)-propionitrile was precipitated using 12.8 ml of 3.6N isopropanolic hydrochloric acid (colourless crystals, m.p. 186°–190° C., 6.68 g).

This intermediate was hydrogenated in 31 ml of 25% HCl and 31 ml of glacial acetic acid in the presence of 0.13 g of platinum dioxide at RT under 10 bar. After evaporation of the hydrogenation solution, the residue was taken up in 50 ml of water, adjusted to pH 13 using concentrated sodium hydroxide solution and extracted with 3×150 ml of ethyl acetate. After distillation, 3-Piperidin-1-yl-propylamine was obtained as a colourless oil, b.p. 45°–50° C./0.1 mm Hg.

Example 40

(R,S)-(7-Chloro-quinolin-4-yl)-(pyrrolidin-3-yl)-amine 9.85 g of 3-aminopyrrolidine were benzoylated with 16 g of benzoyl chloride at 0° C. in 90 ml of dichloromethane, 17.7 ml of N,N-dimethylformamide and 25.5 ml of triethylamine. After warming to room temperature, the mixture was filtered and the filtrate was evaporated to dryness. The residue was taken up in 100 ml of water (pH 8), filtered and again evaporated to dryness. The residue was digested in succession with in each case 90 ml of toluene, ethyl acetate and dichloromethane, the solution being decanted off each time from initially oily, but later crystalline, residue. The organic solutions were combined and evaporated. The dark colored off obtained (2.7 g) was then reacted at 140° C. overnight with 2.1 g of 4,7-dichloroquinoline and 2.1 g of phenol. The reaction mixture was taken up with 50 ml of water, adjusted to pH 2 by the addition of conc. hydrochloric acid, and extracted three times with 50 ml of ethyl acetate each time. Thereafter, the aqueous phase was adjusted to pH 12 using conc. sodium hydroxide solution and extracted three times with 50 ml of ethyl acetate each time. After evaporation of the solvent, the residue was crystallized from 10 ml of ethyl acetate/toluene. The resulting product (0.6 g) was then saponified to (R,S)-(7-chloro-quinolin-4-yl)-(pyrrolidin-3-yl)-amine dihydrobromide by boiling in 10 ml of 48% HBr for 12 hours.

Example 41

$N_1$-(7-Chloro-quinolin-4-yl)-2-methyl-propane-1,2-diamine 52.8 g of 4,7-dichloroquinoline and 30.85 g of 1,2-diamino-2-methylpropane were stirred in 530 ml of N-methyl-2-pyrrolidone under argon at 150° C. for 5 hours. Thereafter, the solvent was evaporated in a vacuum and the residue was taken up in 1250 ml of water. After adjustment to pH 1 using conc. hydrochloric acid, the mixture was extracted once with 200 ml of ethyl acetate and twice with 100 ml of ethyl acetate each time, and subsequently treated with about 170 ml of 30% potassium hydroxide solution until the pH reached 12. Thereby, 88 g of $N_1$-(7-chloro-quinolin-4-yl)-2-methyl-propane-1,2-diamine separate out in crystalline form; m.p.: 169°–171° C.

Example 42

(S)-2-Amino-1-chloro-N-(7-chloro-quinolin-4-yl)-propane 23 g of L-alaninol and 57.4 g of 4,7-dichloroquinoline in 100 ml of 1-methyl-2-pyrrolidone were held at 150° C. for 6 hrs. After cooling, the reaction mixture was poured into 500 ml of cold 2N HCl and extracted with 3×200 ml of dichloromethane. The acidic-aqueous phase was made basic with 28% NaOH resulting in precipitation of the crude product. After stirring in an ice bath for 30 min., the product was filtered off and then recrystallized from 300 ml of 2-propanol/150 ml of ethanol. We obtained 51.2 g (74%) of (S)-2-amino-N-(7-chloro-qulnolin-4-yl)-1-propanol; white crystals, m.p.: 225° C., $[a]_D = +35°$ (c=1.0, MeOH).

$^1$H-NMR (250 MHz) in d$_6$-DMSO, signals at δ (ppm): 1.24 (d, J=6.4, 3H), 3.45 (m, 1H), 3.58 (m, 1H), 3.73 (m, 1H), 4.87 (t, J=5.6, 1H), 6.53 (d, J=7, 1H), 6.84 (d, J=7.7, 1H), 7.44 (dd, J$_1$=9, J$_2$2, 1H), 7.78 (d, J=2, 1H), 8.35 (d, J=7, 1H), 8.39 (d, J=9, 1H)

27.3 g of (S)-2-amino-N-(7-chloro-quinolin-4-yl)-1-propanol were suspended in 270 ml of chloroform. Then, a solution of 72 ml of thionyl chloride in 70 ml of chloroform was added dropwise over 30 min. while cooling with ice (the temperature was maintained below 25° C.). Subsequently, the mixture was stirred at room temperature for a further 30 min. and at 70° C. for 90 min. The reaction mixture was cooled and evaporated, then treated with toluene and again evaporated. The resulting foam was dissolved in 500 ml of ethanol while warming, filtered and concentrated to about 300 ml, whereupon crystallization occurred. We obtained 31.6 g (94%) of (S)-2-amino-1-chloro-N-(7-chloro-quinolin-4-yl)-propane hydrochloride as white crystals; m.p.: 210° C., [a]$_D$=+90° (c=1.0, MeOH).

The R enantiomer, (R)-2-amino-1-chloro-N-(7-chloro-quinolin-4-yl)-propane, was obtained as the hydrochloride starting from D-alaninol; white crystals, m.p.: 210° C., [a]$_D$=−88° (c=1.0, MeOH).

$^1$H-NMR (250 MHz) in d$_6$-DMSO, signals at δ (ppm): 1.41 (d, J=6.5, 3H), 3.88–4.06 (m, 2H), 4.48 (m, 1H), 7.03 (d, J=7.3, 1H), 7.79 (dd, J$_1$=9, J$_2$=2, 1H), 8.15 (d, J=2, 1H), 8.59 (d, J=7.3, 1H), 8.89 (d, J=9, 1H), 9.44 (d, J=8.4, 1H), 14.66 (s, 1H)

Example 43

(S)-N$_2$,N$_2$-Dimethyl-1,2-propanediamine 7.6 g of L-alaninol were stirred at 90° C. for 14 hrs. in 20 ml of formic acid and 20 ml of 37% formaldehyde solution. After cooling the reaction mixture was poured on to 100 g of ice and 60 ml of 28% NaOH and extracted with 3×100 ml of dichloromethane. After drying and evaporating the dichloromethane phases, the crude produce was distilled at normal pressure. We obtained 7.8 g of (S)-2-dimethylamino-1-propanol as a colorless oil; b.p. 147° C., [a]$_D$=+2.7° (c=1.0, MeOH).

7.3 g of (S)-2-dimethylamino-1-propanol, 37 g of triphenylphospine and 20.8 g of phthalimide were suspended in 70 ml of tetrahydrofuran under argon and cooled in an ice bath. Then, 24 ml of diethyl azodicarboxylate were added dropwise over 30 min. and the mixture was stirred at room temperature for a further 5 hrs. Then, the mixture was poured into 200 ml of ice-cold 1N HCl and extracted with 3×200 ml of ethyl acetate. The acidic-aqueous phase was made basic with 28% NaOH and then extracted with 3×200 ml of dichloromethane. After drying and evaporating the dichloromethane phases, the crude product (12 g GC 78%+ 16% regioisomer) was chromatographed on silica gel in ethyl acetate. We obtained 6 g of yellow oil which solidified (regioisomer not separated). This 6 g of product were boiled at reflux in 50 ml of conc. HCl for 20 hrs. After cooling the precipitated phthalic acid was filtered off. The filtrate was washed with 2×50 ml of dichloromethane and then made basic cautiously with solid KOH while cooling in an ice bath and finally extracted with 3×80 ml of dichloromethane. After drying and evaporating the dichloromethane phases the crude product was distilled at normal pressure. This resulted in 1.2 g of (S)-N$_2$,N$_2$-dimethyl-1,2-propanediamine as a colorless oil; b.p.: 127° C.

$^1$H-NMR (250 MHz) in CDCl$_3$, signals at δ (ppm): 0.89 (d, J=6.4, 3H), 1.37 (s, 2H), 2.22 (s, 6H), 2.48–2.67 (m, 3H)

The R enantiomer, (R)-N$_2$,N$_2$-dimethyl-1,2-propanediamine, is prepared in an analogous manner starting from D-alaninol.

Example A (RS)-N$_2$-(7-Chloro-quinolin-4-yl)-N$_1$,N$_1$-dimethyl-propane-1,2-diamine is formulated as the active ingredient in pharmaceutical preparations according to methods well known in the art. Examples of tablet, capsule, suppository and gelatine capsule formulations are provided below:

| 1. 500 mg tablets | |
|---|---|
| Active ingredient | 500 mg |
| Powd. lactose. | 149 mg |
| Polyvinylpyrrolidone | 15 mg |
| Dioctyl sodium sulphosuccinate | 1 mg |
| Na carboxymethylstarch | 30 mg |
| Magnesium stearate | 5 mg |
| | 700 mg |
| 2. 50 mg tablets | |
| Active ingredient | 50 mg |
| Powd. lactose | 50 mg |
| Microcrystalline cellulose | 82 mg |
| Na carboxymethylstarch | 15 mg |
| | 200 mg |
| 3. 100 mg capsules | |
| Active ingredient | 100.0 mg |
| Powd lactose | 104.7 mg |
| Corn starch | 70.0 mg |
| Hydroxypropylmethylcellulose | 10.0 mg |
| Dioctyl sodium sulphosuccinate | 0.3 mg |
| Talc | 12.0 mg |
| Magnesium stearate | 3.0 mg |
| | 300.0 mg |
| 4. 500 mg suppositories | |
| Active ingredient | 500 mg |
| Suppository mass | ad 2000 mg |
| 5. 100 mg soft gelatine capsules | |
| Active ingredient | 100 mg |
| Medium chain triglyceride | 300 mg |
| | 400 mg |

We claim:
1. A method for the treatment of chloroquine-resistant malaria comprising administering to a patient a composition containing a therapeutically effective amount of a an aminoquinoline derivative of general formula

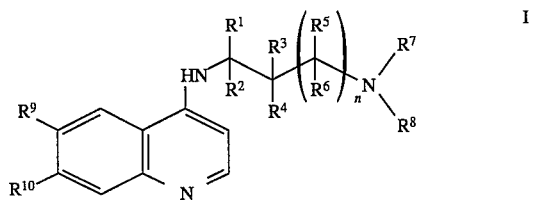

wherein R$^1$ to R$^6$ are hydrogen or in which one or two of R$^1$ to R$^6$ are independently selected from alkyl and the other substituents are hydrogen; R$^7$ and R$^8$ are independently selected from alkyl, alkenyl or aralkyl, or together with the N atom signify pyrrolidine or piperidine, either or both of which may be substituted by alkyl; and n=0 or 1; or wherein $R^1$ and $R^3$ are tri- or tetramethylene; $R^2$ and $R^4$ to $R^6$ are hydrogen; n=0; and $R^7$ and $R^8$ are defined as above; or wherein $R^1$ and $R^7$ are methylene or dimethylene and n=1, or $R^3$ and $R^7$ are di- or trimethylene and n=0, or $R^3$ and $R^7$ are di- or trimethylene and n=1, or $R^3$ and $R^7$ are tri- or tetramethylene and n=0, or $R^5$ and $R^7$ are tri- or tetramethylene and n=1, or $R^1$ and $R^5$ are di- or tri-methylene and n=1, and the remaining substituents are hydrogen, except $R^8$ which is selected from alkyl, alkenyl or alkynyl; or wherein $R^3$ and $R^5$ are tri-or tetramethylene and n=1; $R^1$, $R^2$, $R^4$ and $R^6$ are hydrogen; and $R^7$ and $R^8$ are selected from alkyl, alkenyl or aralkyl or together with the N atom are pyrrolidine or piperidine, either or both of which may be substituted by alkyl;

$R^9$ is hydrogen or halogen; and $R^{10}$ is halogen or trifluoromethyl, or the pharmaceutically acceptable salts of the above compounds, provided that the aminoquinoline derivatives or formula I do not include:

(7-chloro-quinolin-4-yl)-(2-piperidin-1-yl-ethyl)-amine, (7-chloro-quinolin-4-yl)-[(1-ethyl-pyrrolidin-2-yl)-methyl]-amine, or (RS)(7-chloro-quinolin-4-yl)-(1-methyl-piperidin-2-yl-methyl)-amine.

2. A method for the treatment of chloroquine-resistant malaria comprising administering to a patient a composition containing a therapeutically effective amount of a compound selected from the group consisting of:

$N_2$-(7-chloro-quinolin-4-yl)-$N_1$,$N_1$-dimethyl-ethane-1,2-diamine, $N_2$-(7-chloro-quinolin-4-yl)-$N_1$,$N_1$-diethyl-ethane-1,2-diamine, $N_3$-(7-chloro-quinolin-4-yl)-$N_1$,$N_1$-dimethyl-propane-1,3-diamine, $N_3$-(7-chloro-quinolin-4-yl)-$N_1$,$N_1$-diethyl-propane-1,3-diamine, (RS)(7-chloro-quinolin-4-yl)-(1-methyl-pyrrolidin-2-yl-methyl)-amine, (RS)(7-chloro-quinolin-4-yl)-(1-ethyl-piperidin-3-yl)-amine, or the pharmaceutically acceptable salts of these compounds.

3. A method for the treatment of chloroquine-resistant malaria comprising administering to a patient a composition containing a therapeutically effective amount of at least one compound selected from the group consisting of:

(RS)-$N_2$-(7-chloro-quinolin-4-yl)-$N_1$,$N_1$-dimethyl-propane-1,2-diamine, (RS)-$N_2$-(7-chloro-quinolin-4-yl)-$N_1$,$N_1$-diethyl-propane-1,2-diamine, (S)-$N_2$-(7-chloro-quinolin-4-yl)-$N_1$,$N_1$-diethyl-propane-1,2-diamine, (R)-$N_2$-(7-chloro-quinolin-4-yl)-$N_1$,$N_1$-diethyl-propane-1,2-diamine, (RS)-(7-chloro-quinolin-4-yl)-(1-methyl-2-pyrrolidin-1-yl-ethyl)-amine, (R)-$N_1$-(7-chloro-quinolin-4-yl)-$N_2$,$N_2$-dimethyl-propane-1,2-diamine, (S)-$N_1$-(7-chloro-quinolin-4-yl)-$N_2$,$N_2$-dimethyl-propane-1,2-diamine, or the pharmaceutically acceptable salts of these compounds.

4. A method for the treatment of chloroquine-resistant malaria comprising administering to a patient a composition containing a therapeutically effective amount of at least one compound selected from the group consisting of:

(S)-$N_2$-(7-chloro-quinolin-4-yl)-$N_1$,$N_1$-dimethyl-propane-1,2-diamine, (R)-$N_2$-(7-chloro-quinolin-4-yl)-$N_1$,$N_1$-dimethyl-propane-1,2-diamine, $N_1$-(7-chloro-quinolin-4-yl)-2,$N_2$,$N_2$-trimethyl-propane-1,2-diamine, (RS)-(7-chloro-quinolin-4-yl)-(1-methyl-pyrrolidin-3-yl)-amine, or the pharmaceutically acceptable salts of these compounds.

5. The method of claim 1 wherein said composition is administered orally.

6. The method of claim 5 wherein said composition is administered such that the patient receives a daily dose of from about 1 mg. to about 50 mg. per kg. body weight of a compound of formula I, or its pharmaceutically acceptable salts thereof.

7. The method of claim 1 wherein said therapeutically effective amount is from about 1 mg. to about 50 mg. per Kg. body weight per day.

8. The method of claim 3 wherein said therapeutically effective amount is from about 1 mg. to about 50 mg. per Kg. body weight per day.

9. The method of claim 3 wherein said therapeutically effective amount is from about 1 mg. to about 50 mg. per Kg. body weight per day.

10. The method of claim 4, wherein said composition contains in addition at least one other pharmaceutically active ingredient.

* * * * *

UNITED STATES PATENT AND TRADEMARK OFFICE
CERTIFICATE OF CORRECTION

PATENT NO. : 5,596,002
DATED : Jan. 21, 1997
INVENTOR(S) : Werner Hofheinz, Catherine Jaquet, Synèse Jolidon It is certified that error appears in the above-indentified patent and that said Letters Patent is hereby corrected as shown below:

In claim 1, column 27, line 6, change "$R^3$" to -- $R^1$ --.

In claim 9, column 28, line 45 change "The method of claim 3" to -- The method of claim 4 --.

In claim 8, column 28, line 43 change " The method of claim 3" to -- The method of claim 4 --.

Signed and Sealed this

Seventh Day of October, 1997

Attest:

BRUCE LEHMAN

Attesting Officer        Commissioner of Patents and Trademarks